United States Patent
Hayashi et al.

(10) Patent No.: US 12,371,586 B2
(45) Date of Patent: Jul. 29, 2025

(54) PHOTOCURABLE COMPOSITION, THREE-DIMENSIONAL MODELING PRODUCT, AND DENTAL PRODUCT

(71) Applicant: MITSUI CHEMICALS, INC., Tokyo (JP)

(72) Inventors: Takaaki Hayashi, Funabashi (JP); Toshikazu Sakamaki, Tokyo (JP); Mai Kimura, Sodegaura (JP); Hiroki Murai, Ichihara (JP); Suguru Endo, Ichikawa (JP); Eiji Kobayashi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 358 days.

(21) Appl. No.: 18/004,185

(22) PCT Filed: Jul. 6, 2021

(86) PCT No.: PCT/JP2021/025460
§ 371 (c)(1),
(2) Date: Jan. 4, 2023

(87) PCT Pub. No.: WO2022/009880
PCT Pub. Date: Jan. 13, 2022

(65) Prior Publication Data
US 2023/0242785 A1    Aug. 3, 2023

(30) Foreign Application Priority Data
Jul. 7, 2020    (JP) .................... 2020-117229

(51) Int. Cl.
| C08F 2/46 | (2006.01) |
| A61C 13/34 | (2006.01) |
| B33Y 70/00 | (2020.01) |
| C08F 2/50 | (2006.01) |
| C08F 222/10 | (2006.01) |
| C08G 61/04 | (2006.01) |
| C09D 4/00 | (2006.01) |
| C09D 7/63 | (2018.01) |
| C09D 135/02 | (2006.01) |
| B33Y 80/00 | (2015.01) |

(52) U.S. Cl.
CPC ............ *C09D 135/02* (2013.01); *A61C 13/34* (2013.01); *B33Y 70/00* (2014.12); *C08F 222/1025* (2020.02); *C08F 222/103* (2020.02); *C08F 222/104* (2020.02); *C09D 4/00* (2013.01); *C09D 7/63* (2018.01); *B33Y 80/00* (2014.12)

(58) Field of Classification Search
CPC .......... C09D 135/02; C09D 4/00; C09D 7/63; B33Y 70/00; B33Y 80/00; B33Y 10/00; C08L 33/08; C08L 33/10; A61K 6/887; C08F 222/104; C08F 222/1025; C08F 222/1806; C08F 222/1811; C08F 222/102; A61C 13/34; A61C 7/08; B29C 64/124; B29L 2031/7536
USPC .................. 522/64, 6, 71, 1, 189, 184; 520/1
See application file for complete search history.

(56) References Cited

U.S. PATENT DOCUMENTS

| 2002/0127345 A1 | 9/2002 | Rheinberger et al. |
| 2014/0239527 A1 | 8/2014 | Lee |
| 2016/0062016 A1* | 3/2016 | Lee ...................... C09D 133/14 522/64 |
| 2017/0172855 A1 | 6/2017 | Moszner et al. |
| 2017/0360534 A1 | 12/2017 | Sun et al. |
| 2018/0258297 A1 | 9/2018 | Kitou et al. |

FOREIGN PATENT DOCUMENTS

| JP | 2008189782 A | 8/2008 |
| JP | 4160311 B2 | 10/2008 |
| JP | 2012102226 A * | 5/2012 |
| JP | 2016525150 A | 8/2016 |
| JP | 2019521188 A | 7/2019 |
| WO | 2016/005534 A1 | 1/2016 |
| WO | 2016/149488 A1 | 9/2016 |
| WO | 2017047693 A1 | 3/2017 |
| WO | 2018105463 A1 | 6/2018 |

OTHER PUBLICATIONS

Akama et al, JP 2012102226 Machine Translation, May 31, 2012 (Year: 2012).*

* cited by examiner

*Primary Examiner* — Jessica Whiteley
(74) *Attorney, Agent, or Firm* — BUCHANAN INGERSOLL & ROONEY PC

(57) ABSTRACT

A photocurable composition, wherein: in a case in which a rectangular sheet-like test piece P1 with a length of 40 mm, a width of 10 mm, and a thickness of 0.5 mm is produced by photomodeling under specific conditions, and a storage modulus is measured for the thus produced test piece P1 by dynamic viscoelastic measurement with a measurement frequency of 1 Hz while increasing a temperature in a range of from 25° C. to 300° C. at a rate of 3° C./min, the storage modulus at 135° C. is $3.0 \times 10^8$ Pa or more.

11 Claims, 1 Drawing Sheet

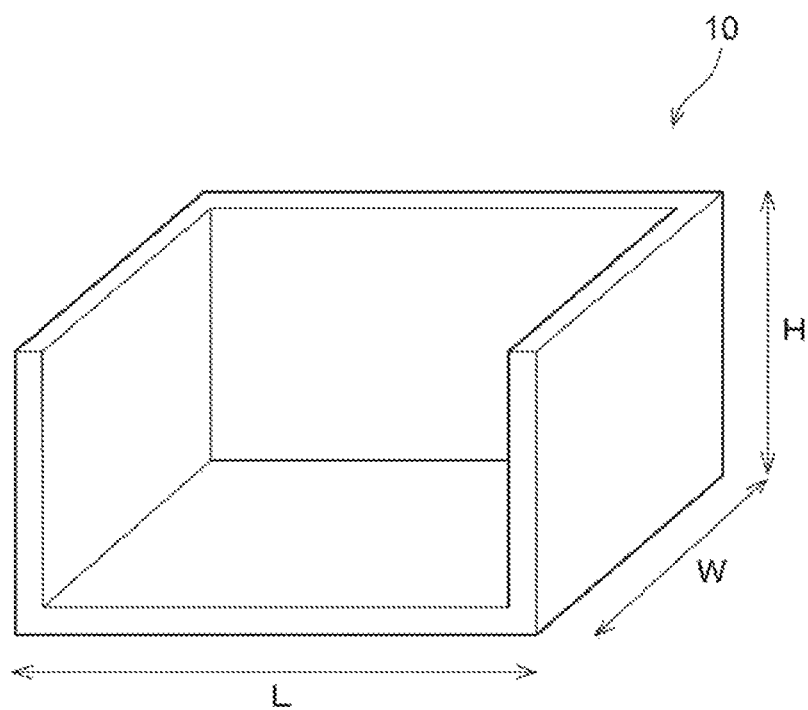

PHOTOCURABLE COMPOSITION, THREE-DIMENSIONAL MODELING PRODUCT, AND DENTAL PRODUCT

TECHNICAL FIELD

The present disclosure relates to a photocurable composition, a three-dimensional modeling product, and a dental product.

BACKGROUND ART

Dental products such as dental prostheses and instruments for intraoral use have been studied in recent years. For example, in terms of the efficiency of modeling these dental products, methods of producing a three-dimensional modeling product such as a dental product by photomodeling using a 3D printer have been known (see, for example, Patent Document 1).

Patent Document 1: Japanese Patent No. 4160311

SUMMARY OF INVENTION

Technical Problem

Incidentally, a dental product (e.g., a dental surgical guide, a mouthpiece, or a dental model) is used after being heat-sterilized in some cases. When a three-dimensional modeling product, which is a cured product of a photocurable composition, is used as at least a part of such a dental product, the dimensional accuracy of the three-dimensional modeling product may be deteriorated due to deformation caused by heat sterilization.

Accordingly, the three-dimensional modeling product, which is a cured product of a photocurable composition and used as at least a part of a dental product, is sometimes required to have a dimensional accuracy after heat sterilization.

Further, a cured product (three-dimensional modeling product) of a photocurable composition, which is used for an application other than a dental product, may also be required to have a dimensional accuracy after heating (e.g., after heat sterilization).

An object of one aspect of the disclosure is to provide: a photocurable composition from which a three-dimensional modeling product exhibiting an excellent dimensional accuracy after heating can be produced; and a three-dimensional modeling product and a dental product which exhibit an excellent dimensional accuracy after heating.

Solution to Problem

Means for solving the above-described problems include the following aspects.

<1> A photocurable composition, comprising a photopolymerizable component and a photopolymerization initiator, wherein:

in a case in which a rectangular sheet-like test piece P1 with a length of 40 mm, a width of 10 mm, and a thickness of 0.5 mm is produced by photomodeling under conditions in which the photocurable composition is irradiated with visible light having a wavelength of 405 nm at an irradiation dose of 11 mJ/cm$^2$ to form a cured layer P1 with a thickness of 50 μm, the cured layer P1 is stacked in a thickness direction thereof to form a rectangular sheet-like modeling product P1 with a length of 40 mm, a width of 10 mm, and a thickness of 0.5 mm, and the modeling product P1 is irradiated with ultraviolet rays having a wavelength of 365 nm at an irradiation dose of 3 J/cm$^2$ to produce the test piece P1, and a storage modulus is measured for the thus produced test piece P1 by dynamic viscoelastic measurement with a measurement frequency of 1 Hz while increasing a temperature in a range of from 25° C. to 300° C. at a rate of 3° C./min, the storage modulus at 135° C. is 3.0×10$^8$ Pa or more.

<2> The photocurable composition according to <1>, wherein the storage modulus at 135° C. is 3.5×10$^9$ Pa or less.

<3> The photocurable composition according to <1> or <2>, wherein the photopolymerizable component comprises at least one of:

a di(meth)acrylic monomer (A) which comprises two (meth)acryloyloxy groups and a cyclic structure, and has a distance of 15.0 Å or more between an oxygen atom forming an oxy group in one of the (meth)acryloyloxy groups and an oxygen atom forming an oxy group in another of the (meth)acryloyloxy groups;

a di(meth)acrylic monomer (B) which comprises two (meth)acryloyloxy groups, and has a distance of less than 15.0 Å between an oxygen atom forming an oxy group in one of the (meth)acryloyloxy groups and an oxygen atom forming an oxy group in another of the (meth)acryloyloxy groups; or a poly(meth)acrylic monomer (C) which comprises three or more (meth)acryloyloxy groups.

<4> The photocurable composition according to <3>, wherein the photopolymerizable component comprises:

two kinds of the di(meth)acrylic monomer (A) that are different in the distance between the oxygen atom forming an oxy group in the one of the (meth)acryloyloxy groups and the oxygen atom forming an oxy group in another of the (meth)acryloyloxy groups; or the di(meth)acrylic monomer (A), and at least one of a mono(meth)acrylic monomer (D), which comprises one (meth)acryloyloxy group and at least one of a branched structure or a cyclic structure, or the di(meth)acrylic monomer (B).

<5> The photocurable composition according to <3>, wherein the photopolymerizable component comprises the di(meth)acrylic monomer (B) and includes:

two or more kinds of the di(meth)acrylic monomer (B), a mono(meth)acrylic monomer comprising one (meth)acryloyloxy group, a di(meth)acrylic monomer other than the di(meth)acrylic monomer (B), which comprises two (meth)acryloyloxy groups, or any combination thereof.

<6> The photocurable composition according to <3>, wherein the photopolymerizable component comprises:

the poly(meth)acrylic monomer (C); and at least one of a mono(meth)acrylic monomer comprising one (meth)acryloyloxy group or a di(meth)acrylic monomer comprising two (meth)acryloyloxy groups.

<7> The photocurable composition according to any one of <3> to <6>, wherein a total content of the di(meth)acrylic monomer (A), the di(meth)acrylic monomer (B), and the poly(meth)acrylic monomer (C) is 50% by mass or more with respect to a total amount of (meth)acrylic monomer components.

<8> The photocurable composition according to any one of <1> to <3>, wherein the photopolymerizable component comprises:

a di(meth)acrylic monomer (X) which comprises two (meth)acryloyloxy groups and a cyclic structure, and has a distance of 17.0 Å or more between an oxygen atom forming an oxy group in one of the (meth)acryloyloxy groups and an oxygen atom forming an oxy group in another of the (meth)acryloyloxy groups; and a di(meth)acrylic monomer (Y) which comprises two (meth)acryloyloxy groups, and has a distance of less than 17.0 Å between an oxygen atom forming an oxy group in one of the (meth)acryloyloxy groups and an oxygen atom forming an oxy group in another of the (meth)acryloyloxy groups.

<9> The photocurable composition according to <8>, wherein a total content of the di(meth)acrylic monomer (X) and the di(meth)acrylic monomer (Y) is 50% by mass or more with respect to a total amount of (meth)acrylic monomer components.

<10> The photocurable composition according to <8> or <9>, wherein a content of the di(meth)acrylic monomer (X) is from 50% by mass to 90% by mass with respect to a total amount of (meth)acrylic monomer components.

<11> The photocurable composition according to any one of <8> to <10>, wherein a content of the di(meth)acrylic monomer (Y) is from 10% by mass to 50% by mass with respect to a total amount of (meth)acrylic monomer components.

<12> The photocurable composition according to any one of <1> to <9>, having a viscosity, which is measured by an E-type viscometer under conditions of 25° C. and 50 rpm, of from 5 mPa·s to 6,000 mPa·s.

<13> The photocurable composition according to any one of <1> to <12>, which is a photocurable composition for photomodeling.

<14> The photocurable composition according to any one of <1> to <13>, which is used for production of a dental product by photomodeling.

<15> A three-dimensional modeling product, which is a cured product of the photocurable composition according to any one of <1> to <14>.

<16> A dental product, comprising the three-dimensional modeling product according to <15>.

<17> The dental product according to <16>, which is a dental surgical guide, a dental tray, a mouthpiece, or a dental model.

Advantageous Effects of Invention

According to one aspect of the disclosure, the followings are provided: a photocurable composition from which a three-dimensional modeling product exhibiting an excellent dimensional accuracy after heating (e.g., after heat sterilization; the same applies below) can be produced; and a three-dimensional modeling product and a dental product which exhibit an excellent dimensional accuracy after heating.

BRIEF DESCRIPTION OF DRAWING

FIG. 1 is a schematic perspective view that illustrates one example of the three-dimensional modeling product according to the disclosure.

DESCRIPTION OF EMBODIMENTS

In the disclosure, those numerical ranges that are expressed with "to" each denote a range that includes the numerical values stated before and after "to" as the lower limit value and the upper limit value, respectively.

In the disclosure, when there are plural substances that correspond to a component of a composition, the indicated amount of the component in the composition means, unless otherwise specified, a total amount of the plural substances existing in the composition.

In a set of numerical ranges that are stated in a stepwise manner in the disclosure, the upper limit value or the lower limit value of one numerical range may be replaced with the upper limit value or the lower limit value of other numerical range. Further, in a numerical range stated in the disclosure, the upper limit value or the lower limit value of the numerical range may be replaced with a relevant value indicated in any of Examples.

In the disclosure, "light" is a concept that encompasses active energy rays such as ultraviolet rays and visible light beams.

In the disclosure, "(meth)acrylate" refers to an acrylate or a methacrylate, "(meth)acryloyl" refers to acryloyl or methacryloyl, and "(meth)acryl" refers to acryl or methacryl.

The photocurable composition of the disclosure is a photocurable composition containing a photopolymerizable component and a photopolymerization initiator, wherein:

in a case in which a rectangular sheet-like test piece P1 with a length of 40 mm, a width of 10 mm, and a thickness of 0.5 mm is produced by photomodeling under conditions in which the photocurable composition is irradiated with visible light having a wavelength of 405 nm at an irradiation dose of 11 mJ/cm$^2$ to form a cured layer P1 with a thickness of 50 μm, the cured layer P1 is stacked in a thickness direction thereof to form a rectangular sheet-like modeling product P1 with a length of 40 mm, a width of 10 mm, and a thickness of 0.5 mm, and the modeling product P1 is irradiated with ultraviolet rays having a wavelength of 365 nm at an irradiation dose of 3 J/cm$^2$ to produce the test piece P1, and a storage modulus is measured for the thus produced test piece P1 by dynamic viscoelastic measurement with a measurement frequency of 1 Hz while increasing a temperature in a range of from 25° C. to 300° C. at a rate of 3° C./min, the storage modulus at 135° C. is $3.0 \times 10^8$ Pa or more.

According to the photocurable composition of the disclosure, a three-dimensional modeling product exhibiting an excellent dimensional accuracy after heating can be produced.

The reason why this effect is exerted is believed to be because, with the above-described storage modulus at 135° C. being $3.0 \times 10^8$ Pa or more, a three-dimensional modeling product exhibiting an excellent dimensional accuracy during its production can be produced, and deformation of the thus produced three-dimensional modeling product in the step of heating the three-dimensional modeling product can be inhibited.

The temperature of the heating is preferably from 80° C. to 200° C., more preferably from 100° C. to 180° C., still more preferably from 110° C. to 160° C.

The duration of the heating is preferably from 0.3 minutes to 120 minutes, more preferably from 0.5 minutes to 60 minutes, still more preferably from 1 minute to 20 minutes.

On example of the heating is heat sterilization using an autoclave.

The conditions for the production of a three-dimensional modeling product using the photocurable composition of the disclosure are not particularly limited, and do not necessarily have to be the same as the conditions for the production of the test piece P1. Even when the conditions for the production of a three-dimensional modeling product are different from the conditions for the production of the test piece P1, there is a correlation between the above-described storage modulus at 135° C. and the dimensional accuracy of the three-dimensional modeling product during its production as well as the unlikelihood of the three-dimensional modeling product to be deformed at the time of heating.

In other words, the storage modulus at 135° C. is an index of the dimensional accuracy of a three-dimensional modeling product during its production from the photocurable composition of the disclosure as well as the unlikelihood of the three-dimensional modeling product to be deformed at the time of heating.

A production method employed for the production of a three-dimensional modeling product using the photocurable composition of the disclosure is preferably photomodeling. In this case, the correlation between the storage modulus at 135° C. and the dimensional accuracy of the three-dimensional modeling product during its production as well as the unlikelihood of the three-dimensional modeling product to be deformed at the time of heating is enhanced; therefore, the effect of the photocurable composition of the disclosure (i.e., the effect of improving the dimensional accuracy of the resulting three-dimensional modeling product at the time of heating) is exerted more effectively.

That is, the photocurable composition of the disclosure is preferably a photocurable composition for photomodeling and, in other words, a three-dimensional modeling product produced from the photocurable composition of the disclosure is preferably a photomodeling product (i.e., a cured product obtained by photomodeling).

Photomodeling is a method of obtaining a cured product (i.e., a photomodeling product) by repeating an operation of irradiating a photocurable composition with light to form a cured layer and thereby disposing the cured layer on one another.

The photomodeling may be inkjet photomodeling or vat photomodeling (i.e., photomodeling using a vat).

From the standpoint of allowing the photocurable composition of the disclosure to exert its effect more effectively, the photomodeling is preferably vat photomodeling.

In inkjet photomodeling, a three-dimensional modeling product, which is a cured product of a photocurable composition, is obtained by discharging droplets of the photocurable composition from an inkjet nozzle onto a substrate, and irradiating the droplets adhered to the substrate with light.

In one example of inkjet photomodeling, for example, while scanning a plane with a head equipped with an inkjet nozzle and a light source, a photocurable composition is discharged from the inkjet nozzle onto a substrate and the discharged photocurable composition is irradiated with light to form a cured layer, and these operations are repeated to sequentially dispose cured layers on one another, whereby a cured product (i.e., a photomodeling product) is obtained.

In vat photomodeling, a photocurable composition (i.e., an uncured photocurable composition in a liquid state; the same applies below) housed in a vat is partially cured by photoirradiation to form a cured layer, and the cured layer is disposed on one another by repeating this operation, whereby a cured product (i.e., a photomodeling product) is obtained. Vat photomodeling is different from inkjet photomodeling in that it uses a vat.

Examples of vat photomodeling include DLP (Digital Light Processing) photomodeling and SLA (Stereolithography) photomodeling.

In DLP photomodeling, a photocurable composition in a vat is irradiated with planar light.

In SLA photomodeling, laser light is scanned over a photocurable composition in a vat.

From the standpoint of allowing the photocurable composition of the disclosure to exert its effect more effectively, vat photomodeling is preferably DLP photomodeling.

In one example of DLP photomodeling, for example, a 3D printer (e.g., "CARA PRINT 4.0" manufactured by Kulzer GmbH, or "MAX UV" manufactured by Asiga) that includes the followings is employed:

a vertically movable build table;

a tray (i.e., a vat) which is arranged below the build table (on the side of the gravity direction; the same applies below) and which includes a light transmitting section and houses a photocurable composition; and a light source (e.g., an LED light source) which is arranged below the tray and used for irradiating the photocurable composition in the tray with planar light through the light transmitting section of the tray.

In this example, first, a gap equivalent to a single layer is created between the build table and the tray, and this gap is filled with a photocurable composition. Next, the photocurable composition filling the gap is irradiated with planar light from below through the light transmitting section of the tray to cure the light-irradiated region, whereby a first cured layer is formed. Subsequently, the gap between the build table and the tray is expanded for another layer to be formed next, and the resulting space is filled with the photocurable composition. Then, the photocurable composition filling the space is irradiated with light in the same manner as in the curing of the first layer to form a second cured layer. The above-described operations are repeated to dispose cured layers on one another, whereby a three-dimensional modeling product is produced. In this example, the thus produced three-dimensional modeling product may be further irradiated with light and thereby further cured.

With regard to DLP photomodeling, reference can be made to, for example, Japanese Patent No. 5111880 and Japanese Patent No. 5235056.

<Use>

The use of the photocurable composition of the disclosure is not particularly limited. From the standpoint of further improving the dimensional accuracy of a three-dimensional modeling product at the time of heating, the photocurable composition of the disclosure is preferably a photocurable composition used for the production of a dental product by photomodeling.

The dental product is, for example, a dental prosthesis, a medical instrument for intraoral use, a dental model, or a lost-foam casting model.

Examples of the dental prosthesis include inlays, crowns, bridges, temporary crowns, and temporary bridges.

Examples of the medical instrument for intraoral use include dentures (e.g., complete dentures and partial dentures), mouthpieces (e.g., sports mouthguards and bite splints), orthodontic appliances, impression trays, and dental surgical guides.

Examples of the dental model include jaw models.

The photocurable composition of the disclosure may also be used for the production of an industrial product other than a dental product, and can be used for, for example, a chassis or component of a molding die, an automobile, a home electric appliance, or a precision instrument, or prototyping of such a chassis or component.

As the dental product,
a dental product which is used after being heated is preferred,
a dental surgical guide, a mouthpiece, or a dental model, which is used after being heated and is particularly strongly demanded to have an excellent post-heating dimensional accuracy, is more preferred, and
a dental surgical guide which is used after being heat-sterilized and is particularly strongly demanded to have an excellent post-heat-sterilization dimensional accuracy is particularly preferred.

<Storage Modulus at 135° C.>

As described above, when the storage modulus is measured for the test piece P1 produced from the photocurable composition of the disclosure by dynamic viscoelastic measurement with a measurement frequency of 1 Hz while increasing the temperature in a temperature increase range of from 25° C. to 300° C. at a temperature increase rate of 3° C./min, the storage modulus at 135° C. is $3.0 \times 10^8$ Pa or more.

From the standpoint of further improving the post-heating dimensional accuracy of a three-dimensional modeling product to be produced, the above-described storage modulus at 135° C. is preferably $3.5 \times 10^8$ Pa or more, more preferably $4.0 \times 10^8$ Pa or more, still more preferably $4.5 \times 10^8$ Pa or more.

Meanwhile, an upper limit of the storage modulus at 135° C. is not particularly limited; however, from the standpoint of further improving the toughness of a three-dimensional modeling product to be produced, the upper limit is preferably $3.5 \times 10^9$ Pa, more preferably $3.1 \times 10^9$ Pa, still more preferably $3.0 \times 10^9$ Pa, yet still more preferably $2.0 \times 10^9$ Pa, further preferably $1.0 \times 10^9$ Pa.

From the standpoint of improving the crack resistance of the three-dimensional modeling product (e.g., an improvement of the crack resistance that is required for a dental product), it is advantageous that the three-dimensional modeling product has an excellent toughness.

(Test Piece P1)

The test piece P1 is a rectangular sheet-like test piece of 40 mm in length, 10 mm in width, and 0.5 mm in thickness.

The test piece P1 is produced by photomodeling under conditions in which the photocurable composition of the disclosure is irradiated with visible light having a wavelength of 405 nm at an irradiation dose of 11 mJ/cm² to form a cured layer P1 with a thickness of 50 μm, the cured layer P1 is stacked in a thickness direction thereof to form a rectangular sheet-like modeling product P1 with a length of 40 mm, a width of 10 mm, and a thickness of 0.5 mm, and the modeling product P1 is irradiated with ultraviolet rays having a wavelength of 365 nm at an irradiation dose of 3 J/cm² to produce the test piece P1.

The test piece P1 can be produced, for example, in accordance with the above-described example of DLP photomodeling.

In the below-described Examples, the test piece P1 was produced using "CARA PRINT 4.0" manufactured by Kulzer GmbH, which is a DLP-type 3D printer.

(Storage Modulus at 135° C.)

In the disclosure, the storage modulus at 135° C. is more specifically the storage modulus measured at 135° C. by dynamic viscoelastic measurement with a measurement frequency of 1 Hz while increasing the temperature in a temperature increase range of from 25° C. to 300° C. at a temperature increase rate of 3° C./min.

In the below-described Examples, as an apparatus for the dynamic viscoelastic measurement, a dynamic viscoelasticity analyzer "DVA-225" manufactured by IT Keisoku Seigyo Co., Ltd. was used.

<Photopolymerizable Component>

The photocurable composition of the disclosure contains at least one kind of photopolymerizable component.

The photopolymerizable component is, for example, a compound containing an ethylenic double bond.

Examples of the compound containing an ethylenic double bond include (meth)acrylic monomers, styrene, styrene derivatives, and (meth)acrylonitrile.

As the photopolymerizable component, any of the photopolymerizable components described in the paragraphs [0030] to [0059] of WO 2019/189652 may be used as well.

From the standpoint of further improving the dimensional accuracy of a three-dimensional modeling product to be produced at the time of heating, the content of the photopolymerizable component is preferably not less than 60% by mass, more preferably not less than 80% by mass, still more preferably not less than 90% by mass, with respect to a total amount of the photocurable composition of the disclosure.

The photopolymerizable component preferably contains at least one kind of (meth)acrylic monomer.

The term "(meth)acrylic monomer" used herein means a monomer having one or more (meth)acryloyl groups. The (meth)acrylic monomer is preferably a monomer having one or more (meth)acryloyloxy groups.

In the disclosure, all of (meth)acrylic monomers contained in a photocurable composition may each be referred to as "(meth)acrylic monomer component", and a total amount of all of the (meth)acrylic monomers contained in the photocurable composition of the disclosure may be referred to as "total amount of (meth)acrylic monomer components".

From the standpoint of further improving the dimensional accuracy of a three-dimensional modeling product to be produced at the time of heating, the total amount of (meth)acrylic monomer components is preferably not less than 80% by mass, more preferably not less than 90% by mass, still more preferably not less than 95% by mass, with respect to a total amount of the photopolymerizable component in the photocurable composition of the disclosure.

From the standpoint of further improving the dimensional accuracy of a three-dimensional modeling product to be produced at the time of heating, the total amount of (meth)acrylic monomer components is preferably not less than 60% by mass, more preferably not less than 80% by mass, still more preferably not less than 90% by mass, with respect to a total amount of the photocurable composition of the disclosure.

The (meth)acrylic monomer constituting each (meth)acrylic monomer component may be any monomer as long as it has one or more (meth)acryloyl groups, and there is no other particular limitation.

The (meth)acrylic monomer may be:
a mono(meth)acrylic monomer having one (meth)acryloyl group (hereinafter, also referred to as "monofunctional (meth)acrylic monomer"),
a di(meth)acrylic monomer having two (meth)acryloyl groups (hereinafter, also referred to as "bifunctional (meth)acrylic monomer"), or
a poly(meth)acrylic monomer having three or more (meth)acryloyl groups (hereinafter, also referred to as "polyfunctional (meth)acrylic monomer").

As the mono(meth)acrylic monomer, a mono(meth)acrylic monomer having one (meth)acryloyloxy group is preferred.

As the di(meth)acrylic monomer, a di(meth)acrylic monomer having two (meth)acryloyloxy groups is preferred.

As a tri(meth)acrylic monomer, a poly(meth)acrylic monomer having three or more (meth)acryloyloxy groups is preferred.

The photopolymerizable component preferably contains at least one of:

a di(meth)acrylic monomer (A) which comprises two (meth)acryloyloxy groups and a cyclic structure, and has a distance of 15.0 Å or more between an oxygen atom forming an oxy group in one of the (meth)acryloyloxy groups and an oxygen atom forming an oxy group in another of the (meth)acryloyloxy groups;

a di(meth)acrylic monomer (B) which comprises two (meth)acryloyloxy groups, and has a distance of less than 15.0 Å between an oxygen atom forming an oxy group in one of the (meth)acryloyloxy groups and an oxygen atom forming an oxy group in another of the (meth)acryloyloxy groups; or a poly(meth)acrylic monomer (C) which comprises three or more (meth)acryloyloxy groups.

When this condition is satisfied, a storage modulus at 135° C. of $3.0 \times 10^8$ Pa or more is more likely to be achieved.

(Di(meth)acrylic Monomer (A))

The di(meth)acrylic monomer (A) is a di(meth)acrylic monomer which contains two (meth)acryloyloxy groups and a cyclic structure, and in which the distance between an oxygen atom forming an oxy group in one of the (meth)acryloyloxy groups and an oxygen atom forming an oxy group in another of the (meth)acryloyloxy groups (this distance is hereinafter also referred to as "d1") is 15.0 Å or more.

In the disclosure, the d1 (i.e., the distance between an oxygen atom forming an oxy group in one of the (meth)acryloyloxy groups and an oxygen atom forming an oxy group in another of the (meth)acryloyloxy groups) refers to a linear distance between these two oxygen atoms.

The d1 means a value determined using the "Display Distance Measurement" function of "CHEM 3D" (version 18.2.0.48) manufactured by PerkinElmer Co., Ltd.

An upper limit of the d1 in the di(meth)acrylic monomer (A) is not particularly limited; however, it is, for example, 25.0 Å.

The number of rings in the cyclic structure contained in the di(meth)acrylic monomer (A) may be only one, or two or more.

The cyclic structure contained in the di(meth)acrylic monomer (A) may be either or both of an aromatic ring structure and an alicyclic structure; however, the cyclic structure preferably contains an aromatic ring structure.

The cyclic structure contained in the di(meth)acrylic monomer (A) is particularly preferably a bisphenol A structure.

The di(meth)acrylic monomer (A) may also contain a total of one or more of at least either of an ethyleneoxy group and a propyleneoxy group.

The molecular weight of the di(meth)acrylic monomer (A) is preferably from 400 to 1,000, more preferably from 400 to 800, still more preferably from 400 to 700.

Examples of the di(meth)acrylic monomer (A) include ethoxylated bisphenol A di(meth)acrylate (EO=2 to 4 mol), ethoxylated bisphenol F diacrylate (EO=2 to 4 mol), bisphenol A diglycidyl diacrylate, and propoxylated bisphenol A diacrylate (PO=2 to 4 mol).

The di(meth)acrylic monomer (A) is preferably a dimethacrylic monomer having two methacryloyloxy groups.

(Di(meth)acrylic Monomer (B))

The di(meth)acrylic monomer (B) is a di(meth)acrylic monomer which contains two (meth)acryloyloxy groups, and in which the d1 (i.e., the distance between an oxygen atom forming an oxy group in one of the (meth)acryloyloxy groups and an oxygen atom forming an oxy group in another of (meth)acryloyloxy groups) is less than 15.0 Å.

The d1 in the di(meth)acrylic monomer (B) is preferably 10.0 Å or less.

A lower limit of the d1 in the di(meth)acrylic monomer (B) is not particularly limited; however, it is, for example, 3.0 Å.

The molecular weight of the di(meth)acrylic monomer (B) is preferably from 150 to 400, more preferably from 170 to 350.

Examples of the di(meth)acrylic monomer (B) include neopentyl glycol di(meth)acrylate, ethylene glycol di(meth)acrylate, glycerol di(meth)acrylate, dimethylol-tricyclodecane di(meth)acrylate, and dioxane glycol diacrylate.

(Poly(meth)acrylic Monomer (C))

The poly(meth)acrylic monomer (C) is a poly(meth)acrylic monomer which contains three or more (meth)acryloyloxy groups.

The molecular weight of the poly(meth)acrylic monomer (C) is preferably 5,000 or less, more preferably 3,000 or less, still more preferably 2,500 or less.

A lower limit of the molecular weight of the poly(meth)acrylic monomer (C) is not particularly limited as long as the poly(meth)acrylic monomer (C) is a poly(meth)acrylic monomer having three or more (meth)acryloyloxy groups. The lower limit of the molecular weight of the poly(meth)acrylic monomer (C) is, for example, 200, preferably 250.

Examples of the poly(meth)acrylic monomer (C) include trimethylolpropane tri(meth)acrylate, tetramethylolmethane tetra(meth)acrylate, tri- or higher functional urethane (meth)acrylate, ethoxylated trimethylolpropane triacrylate (EO=3 mol), propoxylated trimethylolpropane triacrylate (PO=3 mol), propoxylated glycerol triacrylate (PO=3 mol), and caprolactone-modified tris(2-acryloxyethyl)isocyanurate triacrylate.

In the photocurable composition of the disclosure, a total content of the di(meth)acrylic monomer (A), the di(meth)acrylic monomer (B), and the poly(meth)acrylic monomer (C) is preferably not less than 30% by mass, more preferably not less than 40% by mass, still more preferably not less than 50% by mass, with respect to a total amount of (meth)acrylic monomer components (i.e., a total amount of all of (meth)acrylic monomers contained in the photocurable composition).

The above-described total content may be 100% by mass, or may be less than 100% by mass (e.g., 95% by mass or less, or 90% by mass or less).

(Mono(meth)acrylic Monomer)

The photopolymerizable component may also contain a mono(meth)acrylic monomer in addition to the above-described at least one of the di(meth)acrylic monomer (A), the di(meth)acrylic monomer (B), or the poly(meth)acrylic monomer (C).

The mono(meth)acrylic monomer is preferably a mono(meth)acrylic monomer having one (meth)acryloyloxy group.

The molecular weight of the mono(meth)acrylic monomer is preferably from 80 to 600, more preferably from 100 to 400, still more preferably from 100 to 300.

The mono(meth)acrylic monomer is more preferably a mono(meth)acrylic monomer (D) which contains one (meth)acryloyloxy group and at least one of a branched structure or a cyclic structure.

Examples of the mono(meth)acrylic monomer (D) (i.e., a mono(meth)acrylic monomer which contains one (meth)acryloyloxy group and at least one of a branched structure or a cyclic structure) include tert-butyl (meth)acrylate, cyclohexyl (meth)acrylate, benzyl (meth)acrylate, phenoxyethyl (meth)acrylate, norbornyl (meth)acrylate, tetrahydrofurfuryl (meth)acrylate, 4-acryloyl morpholine, and dicyclopentanylmethyl (meth)acrylate.

Next, aspects A to C, which are preferred aspects of the photocurable composition of the disclosure, will be described.

It is noted here that at least two of the aspects A to C may have an overlapping part.

(Aspect A)

The aspect A, which is a preferred aspect of the photocurable composition, is an aspect in which the photopolymerizable component contains:

two kinds of the di(meth)acrylic monomer (A) that are different in the above-described distance (d1); or the di(meth)acrylic monomer (A), and at least one of a mono(meth)acrylic monomer having one (meth)acryloyloxy group or a di(meth)acrylic monomer other than the di(meth)acrylic monomer (A), which has two (meth)acryloyloxy groups.

In the aspect A, the content of the di(meth)acrylic monomer (A) is preferably not less than 30% by mass, more preferably not less than 40% by mass, still more preferably not less than 50% by mass, particularly preferably not less than 75% by mass, with respect to a total amount of (meth)acrylic monomer components (i.e., a total amount of all of (meth)acrylic monomers contained in the photocurable composition).

Further, in the aspect A, the content of the di(meth)acrylic monomer (A) may be 90% by mass or less, or 80% by mass or less, with respect to a total amount of (meth)acrylic monomer components.

In the aspect A in which the photopolymerizable component contains two kinds of the di(meth)acrylic monomer (A) that are different in the distance (d1) (this aspect is hereinafter referred to as "aspect A1"), the content of the di(meth)acrylic monomer (A) may be 100% by mass, or may be less than 100% by mass, with respect to a total amount of (meth)acrylic monomer components.

Moreover, in the aspect A, the content of a methacrylic monomer is preferably not less than 50% by mass, more preferably not less than 75% by mass, still more preferably not less than 85% by mass, with respect to a total content of acrylic and methacrylic monomers.

In the aspect A, the mono(meth)acrylic monomer having one (meth)acryloyloxy group is preferably the mono(meth)acrylic monomer (D) (i.e., a mono(meth)acrylic monomer which contains one (meth)acryloyloxy group and at least one of a branched structure or a cyclic structure).

In the aspect A, the di(meth)acrylic monomer other than the di(meth)acrylic monomer (A) is preferably the di(meth)acrylic monomer (B).

In the aspect A, when at least one selected from the group consisting of diethylene glycol dimethacrylate, tripropylene glycol dimethacrylate, and dipropylene glycol diacrylate is contained as the di(meth)acrylic monomer (B), the content of the di(meth)acrylic monomer (A) is preferably not less than 79% by mass, more preferably not less than 80% by mass, with respect to a total amount of (meth)acrylic monomer components. Further, an upper limit of the d1 of the di(meth)acrylic monomer (A) is preferably 18.0 Å.

In the aspect A, when at least one selected from the group consisting of isobornyl acrylate, dicyclopentanyl acrylate, and cyclohexyl acrylate is contained as the di(meth)acrylic monomer (B), the content of a methacrylic monomer is preferably not less than 85% by mass with respect to a total content of acrylic and methacrylic monomers. Further, an upper limit of the d1 of the di(meth)acrylic monomer (A) is preferably 18.0 Å.

In the aspect A, when lauryl acrylate is contained as the di(meth)acrylic monomer (B), the content of a methacrylic monomer is preferably not less than 85% by mass with respect to a total content of acrylic and methacrylic monomers. Further, an upper limit of the d1 of the di(meth)acrylic monomer (A) is preferably 18.0 Å.

—Aspect A1—

The aspect A is preferably the above-described aspect A1 in which two kinds of the di(meth)acrylic monomer (A) different in the distance (d1) are contained.

According to the aspect A1, the post-heating dimensional accuracy and the toughness of a three-dimensional modeling product (e.g., crack resistance required for a dental product) can both be satisfied more effectively.

This is believed to be because not only an effect of improving the post-heating dimensional accuracy is exerted by the di(meth)acrylic monomer (A) having a shorter d1 but also an effect of improving the toughness of a three-dimensional modeling product is exerted by the di(meth)acrylic monomer (A) having a longer d1.

(Aspect B)

The aspect B, which is another preferred aspect of the photocurable composition is an aspect in which the photopolymerizable component contains the di(meth)acrylic monomer (B) and satisfies at least one of the following conditions B1 to B3:

Condition B1: containing two or more kinds of the di(meth)acrylic monomer (B);

Condition B2: containing a mono(meth)acrylic monomer having one (meth)acryloyloxy group; and Condition B3: containing a di(meth)acrylic monomer other than the di(meth)acrylic monomer (B), which has two (meth)acryloyloxy groups.

In the aspect B, the content of the di(meth)acrylic monomer (B) is preferably not less than 30% by mass, more preferably not less than 40% by mass, still more preferably not less than 50% by mass, with respect to a total amount of (meth)acrylic monomer components.

Further, in the aspect B, the content of the di(meth)acrylic monomer (B) is preferably 90% by mass or less, more preferably 80% by mass or less, with respect to a total amount of (meth)acrylic monomer components.

Still further, in the aspect B, the content of a methacrylic monomer is preferably not less than 50% by mass, more preferably not less than 75% by mass, still more preferably not less than 85% by mass, with respect to a total content of acrylic and methacrylic monomers.

Moreover, in the aspect B, the content of a (meth)acrylic monomer having a ring structure is preferably not less than 90% by mass, with respect to a total amount of (meth)acrylic monomer components.

In the aspect B, the mono(meth)acrylic monomer having one (meth)acryloyloxy group is preferably the mono(meth)acrylic monomer (D) (i.e., a mono(meth)acrylic monomer which contains one (meth)acryloyloxy group and at least one of a branched structure or a cyclic structure).

In the aspect B, the di(meth)acrylic monomer other than the di(meth)acrylic monomer (B) is preferably the di(meth)acrylic monomer (A).

In the aspect B, when dimethylol-tricyclodecane dimethacrylate is contained as the di(meth)acrylic monomer (B), the content of a methacrylic monomer is preferably not less than 75% by mass with respect to a total content of acrylic and methacrylic monomers.

In the aspect B, when dimethylol-tricyclodecane dimethacrylate is contained as the di(meth)acrylic monomer (B) and another di(meth)acrylic monomer (B) different from dimethylol-tricyclodecane dimethacrylate is contained, an upper limit of the d1 of the di(meth)acrylic monomer (B) different from dimethylol-tricyclodecane dimethacrylate is preferably 11.0 Å.

(Aspect C)

The aspect C, which is yet another preferred aspect of the photocurable composition is an aspect in which the photopolymerizable component contains:

the poly(meth)acrylic monomer (C); and
at least one of a mono(meth)acrylic monomer having one (meth)acryloyloxy group or a di(meth)acrylic monomer having two (meth)acryloyloxy groups.

In the aspect C, the content of the poly(meth)acrylic monomer (C) is preferably not less than 30% by mass, more preferably not less than 40% by mass, still more preferably not less than 50% by mass, particularly preferably not less than 70% by mass, with respect to a total amount of (meth)acrylic monomer components.

Further, in the aspect C, the content of a methacrylic monomer is preferably not less than 50% by mass, more preferably not less than 70% by mass, still more preferably not less than 80% by mass, with respect to a total content of acrylic and methacrylic monomers.

Moreover, in the aspect C, the content of the poly(meth)acrylic monomer (C) is preferably 90% by mass or less, more preferably 80% by mass or less, with respect to a total amount of (meth)acrylic monomer components.

In the aspect C, the mono(meth)acrylic monomer having one (meth)acryloyloxy group is preferably the mono(meth)acrylic monomer (D) (i.e., a mono(meth)acrylic monomer which contains one (meth)acryloyloxy group and at least one of a branched structure or a cyclic structure).

In the aspect C, the di(meth)acrylic monomer is preferably at least one of the di(meth)acrylic monomer (A) or the di(meth)acrylic monomer (B).

In the aspect C, when at least one selected from the group consisting of polyethylene glycol (400) diacrylate, lauryl acrylate, and 1,12-dodecanediol diacrylate is contained as the di(meth)acrylic monomer (B), the content of a (meth)acrylic monomer having a ring structure is preferably not less than 75% by mass.

In the aspect C, when at least one selected from the group consisting of 1,9-nonanediol diacrylate and cyclohexyl acrylate is contained, or trimethylolpropane triacrylate is contained as the poly(meth)acrylic monomer (C), the content of the poly(meth)acrylic monomer (C) is preferably not less than 75% by mass with respect to a total amount of (meth)acrylic monomer components.

(Aspect XY)

Next, an aspect XY, which is yet another preferred aspect of the photocurable composition of the disclosure, will be described.

The aspect XY is an aspect in which the photopolymerizable component contains:

a di(meth)acrylic monomer (X) which contains two (meth)acryloyloxy groups and a cyclic structure, and has a distance of 17.0 Å or more between an oxygen atom forming an oxy group in one of the (meth)acryloyloxy groups and an oxygen atom forming an oxy group in another of the (meth)acryloyloxy groups; and a di(meth)acrylic monomer (Y) which contains two (meth)acryloyloxy groups, and has a distance of less than 17.0 Å between an oxygen atom forming an oxy group in one of the (meth)acryloyloxy groups and an oxygen atom forming an oxy group in another of the (meth)acryloyloxy group.

There are overlapping parts between the scope of the aspect XY and that of the aspect A1.

Accordingly, some features may correspond to both the aspect XY and the aspect A1, some features may correspond to the aspect XY but not the aspect A1, and some features may correspond to the aspect A1 but not the aspect XY.

According to the aspect XY, an improved post-heating dimensional accuracy and an improved crack resistance required for, for example, a dental product, can be realized more effectively.

This is believed to be because not only an effect of improving the post-heating dimensional accuracy is exerted by the di(meth)acrylic monomer (Y) having a relatively short d1 and the cyclic structure of the di(meth)acrylic monomer (X), but also an effect of improving the crack resistance is exerted by the di(meth)acrylic monomer (X) having a relatively long d1.

—Di(meth)acrylic Monomer (X)—

The di(meth)acrylic monomer (X) is a di(meth)acrylic monomer which contains two (meth)acryloyloxy groups and a cyclic structure, and in which the distance (d1) between an oxygen atom forming an oxy group in one of the (meth)acryloyloxy groups and an oxygen atom forming an oxy group in another of the (meth)acryloyloxy groups is 17.0 Å or more.

The di(meth)acrylic monomer (X) is the above-described di(meth)acrylic monomer (A) in which the d1 is limited to be 17.0 Å or more. Except for this point, preferred aspects of the di(meth)acrylic monomer (X) are the same as those of the above-described di(meth)acrylic monomer (A).

—Di(meth)acrylic Monomer (Y)—

The di(meth)acrylic monomer (Y) is a di(meth)acrylic monomer which contains two (meth)acryloyloxy groups, and in which the d1 (i.e., the distance between an oxygen atom forming an oxy group in one of the (meth)acryloyloxy groups and an oxygen atom forming an oxy group in another of the (meth)acryloyloxy groups) is less than 17.0 Å.

The di(meth)acrylic monomer (Y) is the above-described di(meth)acrylic monomer (B) in which the range of the d1 (less than 15.0 Å) is expanded to less than 17.0 Å. Except for this point, preferred aspects of the di(meth)acrylic monomer (Y) are the same as those of the above-described di(meth)acrylic monomer (B).

Further, the di(meth)acrylic monomer (Y) may have a cyclic structure.

The di(meth)acrylic monomer (Y) having a cyclic structure may correspond to the above-described di(meth)acrylic monomer (A).

A preferred aspect in which the di(meth)acrylic monomer (Y) has a cyclic structure and a d1 of 15.0 Å or more but less than 17.0 Å is the same as a preferred aspect in which the above-described di(meth)acrylic monomer (A) has a d1 of 15.0 Å or more but less than 17.0 Å.

From the standpoint of obtaining the effects of the aspect XY more effectively, in the aspect XY, the total content of the di(meth)acrylic monomer (X) and the di(meth)acrylic monomer (Y) is preferably not less than 30% by mass, more preferably not less than 40% by mass, still more preferably not less than 50% by mass, yet still more preferably not less than 80% by mass, further preferably not less than 90% by mass, yet further preferably not less than 95% by mass, with respect to a total amount of (meth)acrylic monomer components.

In the aspect XY, the ratio of the total content of the di(meth)acrylic monomer (X) and the di(meth)acrylic monomer (Y) with respect to a total amount of (meth)acrylic monomer components may be 100% by mass, or may be less than 100% by mass.

From the standpoint of obtaining the effects of the aspect XY more effectively, in the aspect XY, the content of the di(meth)acrylic monomer (X) is preferably from 50% by mass to 90% by mass with respect to a total amount of (meth)acrylic monomer components.

From the standpoint of obtaining the effects of the aspect XY more effectively, in the aspect XY, the content of the di(meth)acrylic monomer (Y) is preferably from 10% by mass to 50% by mass with respect to a total amount of (meth)acrylic monomer components.

<Photopolymerization Initiator>

The photocurable composition of the disclosure contains at least one kind of photopolymerization initiator.

The photopolymerization initiator is not particularly limited as long as it generates radicals when irradiated with light; however, the photopolymerization initiator is preferably one which generates radicals when irradiated at a wavelength of light used for photomodeling.

The wavelength of light used for photomodeling is generally, for example, from 365 nm to 500 nm; however, from a practical standpoint, it is preferably from 365 nm to 430 nm, more preferably from 365 nm to 420 nm.

Examples of the photopolymerization initiator which generates radicals when irradiated at such a wavelength of light used for photomodeling include alkylphenone compounds, acylphosphine oxide compounds, titanocene compounds, oxime ester compounds, benzoin compounds, acetophenone compounds, benzophenone compounds, thioxanthone compounds, α-acyloxime ester compounds, phenyl glyoxylate compounds, benzil compounds, azo compounds, diphenyl sulfide compounds, organic pigment compounds, ironphthalocyanine compounds, benzoin ether compounds, and anthraquinone compounds.

Thereamong, from the standpoint of reactivity and the like, the photopolymerization initiator is preferably an alkylphenone compound or an acylphosphine oxide compound.

Examples of the alkylphenone compound include 1-hydroxy-cyclohexyl-phenyl-ketone (OMNIRAD 184: manufactured by IGM Resins B.V.).

Examples of the acylphosphine oxide compound include bis(2,4,6-trimethylbenzoyl)-phenyl phosphine oxide (OMNIRAD 819: manufactured by IGM Resins B.V.), and 2,4,6-trimethylbenzoyl-diphenyl phosphine oxide (OMNIRAD TPO: manufactured by IGM Resins B.V.).

The photocurable composition of the disclosure may contain only one kind of photopolymerization initiator, or may contain two or more kinds of photopolymerization initiators.

The content of the photopolymerization initiator in the photocurable composition of the disclosure (a total content when two or more kinds of photopolymerization initiators are contained) is preferably from 0.1% by mass to 10% by mass, more preferably from 0.2% by mass to 5% by mass, particularly preferably from 0.3% by mass to 3% by mass, with respect to a total amount of the photocurable composition.

<Other Components>

If necessary, the photocurable composition of the disclosure may also contain one or more other components in addition to the above-described components.

When the photocurable composition contains other component(s), a total mass of the di(meth)acrylic monomer (A), the acrylic monomer (B), and the photopolymerizable initiator(s) is preferably not less than 30% by mass, more preferably not less than 50% by mass, still more preferably not less than 70% by mass, yet still more preferably not less than 80% by mass, further preferably not less than 90% by mass, with respect to a total amount of the photocurable composition.

Examples of the other components include monomers other than the di(meth)acrylic monomer (A) and the acrylic monomer (B).

When the photocurable composition contains a monomer other than the di(meth)acrylic monomer (A) and the acrylic monomer (B) as other component, the content of the monomer as other component is preferably 50% by mass or less, more preferably 30% by mass or less, still more preferably 20% by mass or less, particularly preferably 10% by mass or less, with respect to a total mass of the di(meth)acrylic monomer (A) and the acrylic monomer (B).

A total content of a hydroxy group-containing (meth)acrylic monomer and a carboxy group-containing (meth)acrylic monomer is preferably 5% by mass or less, more preferably 1% by mass or less, with respect to a total amount of (meth)acrylic monomer components.

Examples of the other components also include: color materials; coupling agents such as silane coupling agents (e.g., 3-acryloxypropyltrimethoxysilane); additives such as rubber agents, ion-trapping agents, ion exchangers, leveling agents, plasticizers, and anti-foaming agents; and thermal polymerization initiators.

When the photocurable composition of the disclosure contains a thermal polymerization initiator, photocuring and heat curing can be employed in combination. Examples of the thermal polymerization initiator include thermal radical generators and amine compounds.

Examples of the other components also include inorganic fillers.

However, from the standpoint of further improving the modeling accuracy of a cured product, the photocurable composition of the disclosure does not contain any inorganic filler (e.g., silica or barium borosilicate glass; the same applies below), or when the photocurable composition of the disclosure contains an inorganic filler, the content thereof with respect to a total amount of the photocurable composition is preferably 60% by mass or less (more preferably 40% by mass or less, still more preferably 20% by mass or less, yet still more preferably 10% by mass or less).

A method of preparing the photocurable composition of the disclosure is not particularly limited.

Examples of the method of preparing the photocurable composition of the disclosure include a method of mixing the di(meth)acrylic monomer (A), the acrylic monomer (B), and the photopolymerization initiator (and other components if necessary).

Means for mixing these components is not particularly limited, and examples thereof include: dissolution by ultrasonic wave; and mixing by a twin-arm stirrer, a roll kneader, a twin-screw extruder, a ball mill kneader, a planetary mixer, or the like.

The photocurable composition of the disclosure may be prepared by mixing the components, subsequently filtering the resultant to remove impurities, and further performing a vacuum degassing treatment of the resultant.

<Preferred Viscosity of Photocurable Composition>

The photocurable composition of the disclosure has a viscosity, which is measured by an E-type viscometer under the conditions of 25° C. and 50 rpm (hereinafter, also simply referred to as "viscosity"), of preferably from 5 mPa·s to 6,000 mPa·s.

It is noted here that "rpm" means revolutions per minute (rotations per minute).

When the viscosity is from 5 mPa·s to 6,000 mPa·s, the photocurable composition has excellent ease of handling in the production of a cured product (particularly a photomodeling product).

The viscosity is more preferably from 10 mPa·s to 5,000 mPa·s, still more preferably from 20 mPa·s to 5,000 mPa·s, yet still more preferably from 50 mPa·s to 1,000 mPa·s.

[Three-Dimensional Modeling Product]

The three-dimensional modeling product of the disclosure is a cured product of the above-described photocurable composition of the disclosure.

Therefore, the three-dimensional modeling product of the disclosure has an excellent post-heating dimensional accuracy.

The three-dimensional modeling product of the disclosure is preferably a cured product obtained by photomodeling (particularly a photomodeling product).

A method of producing the three-dimensional modeling product (e.g., a photomodeling product) is as described above.

[Dental Product]

The dental product of the disclosure includes the above-described three-dimensional modeling product of the disclosure.

Therefore, the dental product of the disclosure has an excellent post-heating dimensional accuracy.

Specific examples of the dental product are as described above.

As described above, as the dental product,
a dental product which is used after being heated is preferred,
a dental surgical guide, a dental tray, a mouthpiece, or a dental model is more preferred, and
a dental surgical guide which is used after being heat-sterilized is particularly preferred.

Preferred ranges of the heating temperature and the heating time in the heat sterilization are as described above.

EXAMPLES

Examples of the disclosure will now be described; however, the disclosure is not limited to the below-described Examples.

Examples 1 to 26 and Comparative Examples 1 and 2

<Production of Photocurable Compositions>

Photocurable compositions were obtained by mixing the respective components as shown in Tables 1 to 3.

<Measurements and Evaluations>

The following measurements and evaluations were performed using the thus obtained photocurable compositions.

The results thereof are shown in Tables 1 and 2.

(Viscosity of Photocurable Compositions)

The viscosity of each of the above-obtained photocurable compositions was measured by an E-type viscometer under the conditions of 25° C. and 50 rpm.

As a result, the photocurable compositions of Examples 1 to 26 were all found to have a viscosity in a range of from 50 mPa·s to 1,000 mPa·s.

(Storage Modulus at 135° C.)

A test piece P1 was produced by the above-described method using each of the above-obtained photocurable compositions, and the storage modulus at 135° C. was measured for the thus obtained test piece P1 by the above-described method.

The production of the test piece P1 was carried out using a DLP-type 3D printer (CARA PRINT 4.0, manufactured by Kulzer GmbH), and the storage modulus at 135° C. was measured using a dynamic viscoelasticity analyzer (DVA-225, manufactured by IT Keisoku Seigyo Co., Ltd.).

(Evaluation of Dimensional Accuracy after Heat Sterilization)

Using a DLP-type 3D printer (CARA PRINT 4.0, manufactured by Kulzer GmbH), a three-dimensional modeling product 10 illustrated in FIG. 1 was produced by DLP photomodeling.

As illustrated in FIG. 1, the three-dimensional modeling product 10 had a shape formed by removing two adjacent faces from the six faces of a hollow cube. The size (design values) of the three-dimensional modeling product 10 was 40 mm in length L, 25 mm in width W, 25 mm in height H, and 2 mm in wall thickness.

The three-dimensional modeling product 10 was produced in the same manner as the test piece P1 by photomodeling under conditions in which each photocurable composition was irradiated with visible light having a wavelength of 405 nm at an irradiation dose of 11 mJ/cm$^2$ to form a cured layer with a thickness of 50 μm, the thus formed cured layer was stacked in a thickness direction thereof to form a modeling product, and this modeling product was irradiated with ultraviolet rays having a wavelength of 365 nm at an irradiation dose of 3 J/cm$^2$.

The length L of the thus produced three-dimensional modeling product 10 was measured to be 40.0 mm using calipers (CD-P15S, manufactured by Mitutoyo Corporation).

The thus obtained three-dimensional modeling product 10 was heat-sterilized in an autoclave at a temperature of 135° C. for 10 minutes.

After this heat sterilization, the length L of the three-dimensional modeling product 10 was measured again using the above-described calipers, and the deviation (mm) from the design value (40 mm) was calculated (Tables 1 to 3).

A smaller deviation from the design value means a superior dimensional accuracy after the heat sterilization.

TABLE 1

| Components of photocurable composition | | | Comparative Example 1 | Comparative Example 2 | Example 1 | Example 2 | Example 3 | Example 4 |
|---|---|---|---|---|---|---|---|---|
| Photopoly-merizable component | Mono(meth)acrylic monomer | TB | | | | 20 | | |
| | | CH | | | | | 20 | |
| | | HO-250 | | 20 | | | | |
| | | BZ | | | | | | 20 |
| | | PO | | | | | | |
| | | IBX | | | | | | |
| | | IBXA | | | | | | |
| | Di(meth)acrylic monomer (A) | SR540 | 80 | | | | | |
| | | SR348 | | 80 | 80 | 80 | 80 | 80 |
| | Di(meth)acrylic monomer (B) | NP | | | | | | |
| | | DCP | | | | | | |
| | | G101P | | | | | | |
| | | EG | | | | | | |
| | | NPA | | | | | | |
| | | DCPA | | | | | | |
| | | A-DOG | | | | | | |
| | Other di(meth)acrylic monomer | UDMA | 20 | | | | | |
| | Poly(meth)acrylic monomer (C) | TMPA | | | | | | |
| | | U15HA | | | | | | |
| | | A-TMMT | | | | | | |
| Photopoly-merization initiator | TPO | | 2 | 2 | 2 | 2 | 2 | 2 |
| | 819 | | | | | | | |
| Storage modulus at 135° C. [Pa] | | | 2.4E+08 | 2.8E+08 | 8.4E+08 | 9.6E+08 | 8.5E+08 | 4.8E+08 |
| Length L after heat sterilization (mm) | | | 39.6 | 39.6 | 39.9 | 39.9 | 39.9 | 39.8 |
| Deviation of length L from design value after heat sterilization (mm) | | | −0.4 | −0.5 | −0.1 | −0.1 | −0.1 | −0.2 |

| Components of photocurable composition | | | Example 5 | Example 6 | Example 7 | Example 8 | Example 9 | Example 10 |
|---|---|---|---|---|---|---|---|---|
| Photopoly-merizable component | Mono(meth)acrylic monomer | TB | | | | | | |
| | | CH | | | | | | |
| | | HO-250 | | | | | | |
| | | BZ | | | | | | |
| | | PO | | | | | | |
| | | IBX | 20 | | | | | |
| | | IBXA | | | | | | |
| | Di(meth)acrylic monomer (A) | SR540 | | | | | | |
| | | SR348 | 80 | 80 | 80 | 80 | 80 | 80 |
| | Di(meth)acrylic monomer (B) | NP | | 20 | | | | |
| | | DCP | | | 20 | | | |
| | | G101P | | | | 20 | | |
| | | EG | | | | | | 20 |
| | | NPA | | | | | | |
| | | DCPA | | | | | | |
| | | A-DOG | | | | | | |
| | Other di(meth)acrylic monomer | UDMA | | | | | | |
| | Poly(meth)acrylic monomer (C) | TMPA | | | | | 20 | |
| | | U15HA | | | | | | |
| | | A-TMMT | | | | | | |
| Photopoly-merization initiator | TPO | | 2 | 2 | 2 | 2 | 2 | 2 |
| | 819 | | | | | | | |
| Storage modulus at 135° C. [Pa] | | | 1.2E+09 | 1.4E+09 | 1.2E+09 | 1.0E+09 | 1.3E+09 | 1.1E+09 |
| Length L after heat sterilization (mm) | | | 40.0 | 40.0 | 40.0 | 39.9 | 39.9 | 39.9 |
| Deviation of length L from design value after heat sterilization (mm) | | | 0.0 | 0.0 | 0.0 | −0.1 | −0.1 | −0.1 |

TABLE 2

| Components of photocurable composition | | | Example 11 | Example 12 | Example 13 | Example 14 | Example 15 | Example 16 | Example 17 |
|---|---|---|---|---|---|---|---|---|---|
| Photopoly-merizable component | Mono(meth)acrylic monomer | TB | | | | | | | |
| | | CH | | | | | | | |
| | | HO-250 | | | | | | | |
| | | BZ | | | | | | | |
| | | PO | | | 20 | | | | |
| | | IBX | | 20 | | | | | |
| | | IBXA | | | | | | 20 | 20 |

TABLE 2-continued

| | | | | | | | | |
|---|---|---|---|---|---|---|---|---|
| Di(meth)acrylic monomer (A) | SR540 | | | | | 80 | 80 | |
| | SR348 | 70 | 80 | 80 | | | | |
| Di(meth)acrylic monomer (B) | NP | 30 | | | 20 | 20 | | |
| | DCP | | | | | | 20 | |
| | G101P | | | | | | | |
| | EG | | | | | | | |
| | NPA | | | | | | 80 | |
| | DCPA | | | | | | | 80 |
| | A-DOG | | | | | | | |
| Other di(meth)acrylic monomer | UDMA | | | | | | | |
| Poly(meth)acrylic monomer (C) | TMPA | | | | | | | |
| | U15HA | | | | | | | |
| | A-TMMT | | | | | | | |
| Photopolymerization initiator | TPO | 2 | | | 2 | 2 | 2 | 2 |
| | 819 | | 2 | 2 | | | | |
| Storage modulus at 135° C. [Pa] | | 1.3E+09 | 1.3E+09 | 1.6E+09 | 6.0E+08 | 5.6E+08 | 1.3E+09 | 8.6E+08 |
| Length L after heat sterilization (mm) | | 39.9 | 40.0 | 40.0 | 39.9 | 39.8 | 40.0 | 39.9 |
| Deviation of length L from design value after heat sterilization (mm) | | −0.1 | 0.0 | 0.0 | −0.1 | −0.2 | 0.0 | −0.1 |

| Components of photocurable composition | | | Example 18 | Example 19 | Example 20 | Example 21 | Example 22 | Example 23 |
|---|---|---|---|---|---|---|---|---|
| Photopolymerizable component | Mono(meth)acrylic monomer | TB | | | | | | |
| | | CH | | | | | | |
| | | HO-250 | | | | | | |
| | | BZ | | | | | | |
| | | PO | | | | | | |
| | | IBX | | 20 | | | | |
| | | IBXA | | | 20 | | 20 | 20 |
| | Di(meth)acrylic monomer (A) | SR540 | | | | | | |
| | | SR348 | | | | | | |
| | Di(meth)acrylic monomer (B) | NP | 20 | 80 | | | | |
| | | DCP | 80 | | | | | |
| | | G101P | | | | | | |
| | | EG | | | | | | |
| | | NPA | | | | | | |
| | | DCPA | | | | 80 | 70 | |
| | | A-DOG | | | | 20 | | |
| | Other di(meth)acrylic monomer | UDMA | | | | | | |
| | Poly(meth)acrylic monomer (C) | TMPA | | | 80 | | | |
| | | U15HA | | | | | 10 | |
| | | A-TMMT | | | | | | 80 |
| Photopolymerization initiator | | TPO | | | | | | |
| | | 819 | 2 | 2 | 2 | 2 | 2 | 2 |
| Storage modulus at 135° C. [Pa] | | | 1.6E+09 | 1.5E+09 | 2.2E+09 | 1.0E+09 | 1.2E+09 | 3.1E+09 |
| Length L after heat sterilization (mm) | | | 40.0 | 40.0 | 40.0 | 39.9 | 39.9 | 40.0 |
| Deviation of length L from design value after heat sterilization (mm) | | | 0.0 | 0.0 | 0.0 | −0.1 | −0.1 | 0.0 |

TABLE 3

| Components of photocurable composition | | | Example 24 | Example 25 | Example 26 |
|---|---|---|---|---|---|
| Photopolymerizable component | Mono(meth)acrylic monomer | TB | | | |
| | | CH | | | |
| | | HO-250 | | | |
| | | BZ | | | |
| | | PO | | | |
| | | IBX | | | |
| | | IBXA | | | |
| | Di(meth)acrylic monomer (A) | SR540 | 50 | 75 | 90 |
| | | SR348 | 50 | 25 | |
| | Di(meth)acrylic monomer (B) | NP | | | |
| | | DCP | | | |
| | | G101P | | | |
| | | EG | | | 10 |
| | | NPA | | | |
| | | DCPA | | | |
| | | A-DOG | | | |

TABLE 3-continued

| Components of photocurable composition | | Example 24 | Example 25 | Example 26 |
|---|---|---|---|---|
| Other di(meth)acrylic monomer | UDMA | | | |
| Poly(meth)acrylic monomer (C) | TMPA | | | |
| | U15HA | | | |
| | A-TMMT | | | |
| Photopolymerization initiator | TPO | | | |
| | 819 | 2 | 2 | 2 |
| Storage modulus at 135° C. [Pa] | | 6.3E+08 | 3.6E+08 | 4.6E+08 |
| Length L after heat sterilization (mm) | | 39.9 | 39.8 | 39.9 |
| Deviation of length L from design value after heat sterilization (mm) | | −0.1 | −0.2 | −0.1 |

In Tables 1 to 3, the numbers in the rows of the respective components each mean an amount in parts by mass, and each blank box means the absence of the corresponding component.

In Tables 1 to 3, the notations such as "8.4E+08" in the row of "Storage modulus at 135° C. [Pa]" mean $8.4 \times 10^8$ and the like.

<Mono(meth)acrylic Monomers>

The mono(meth)acrylic monomers shown in Tables 1 to 3 are as follows.

Among these mono(meth)acrylic monomers, the compounds other than "HO-250" correspond to the mono(meth)acrylic monomer (D).

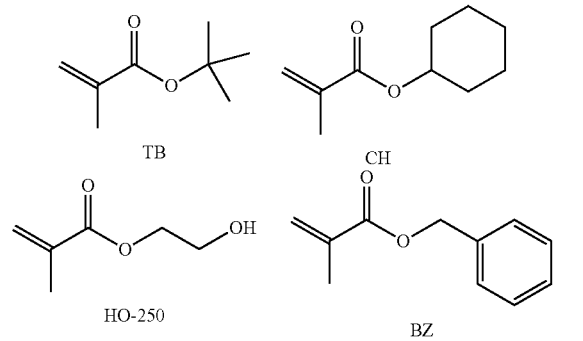

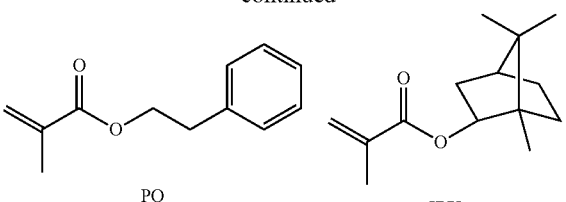

PO
IBX

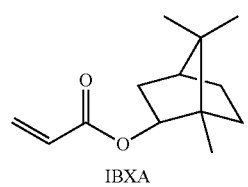

IBXA

<Di(meth)acrylic Monomer (A)>

The di(meth)acrylic monomer (A) shown in Tables 1 to 3 [i.e., di(meth)acrylic monomers which contain two (meth)acryloyloxy groups and a cyclic structure, and in which the d1 (i.e., the distance between an oxygen atom forming an oxy group in one of the (meth)acryloyloxy groups and an oxygen atom forming an oxy group in another of the (meth)acryloyloxy groups) is 15.0 Å or more] are as follows.

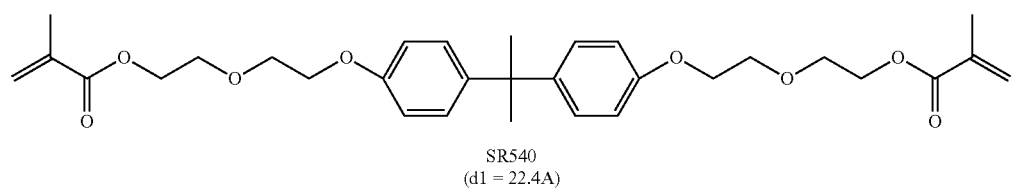

SR540
(d1 = 22.4A)

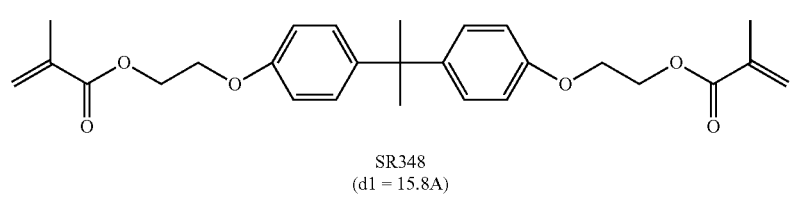

SR348
(d1 = 15.8A)

<Di(meth)acrylic Monomer (B)>

The di(meth)acrylic monomer (B) shown in Tables 1 to 3 [i.e., di(meth)acrylic monomers which contain two (meth)acryloyloxy groups, and in which the d1 (i.e., the distance between an oxygen atom forming an oxy group in one of the (meth)acryloyloxy groups and an oxygen atom forming an oxy group in another of the (meth)acryloyloxy groups) is less than 15.0 Å] are as follows.

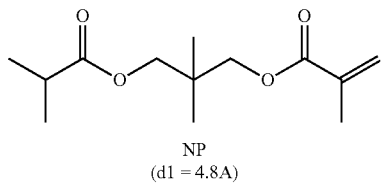

NP
(d1 = 4.8A)

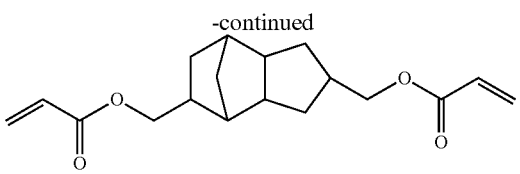

DPA
(d1 = 8.8A)

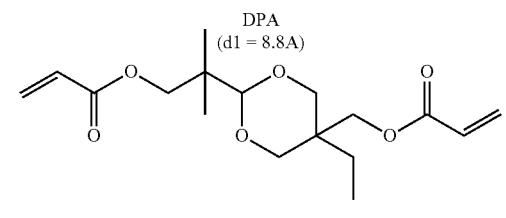

A-DOG
(d1 = 7.8A)

<Other Di(meth)acrylic Monomer>

The other di(meth)acrylic monomer shown in Tables 1 to 3 (i.e., a di(meth)acrylic monomer other than the di(meth)acrylic monomers (A) and (B)) is as follows.

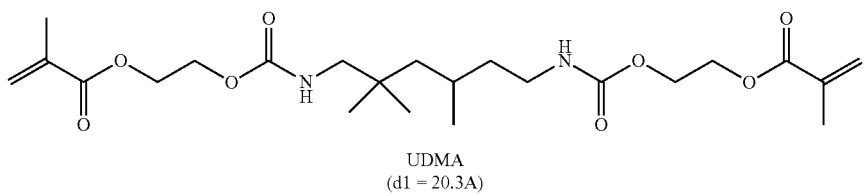 [SMILES: C=C(C)C(=O)OCCOC(=O)NCCC(C)CC(C)(C)CNC(=O)OCCOC(=O)C(=C)C]

UDMA
(d1 = 20.3A)

-continued

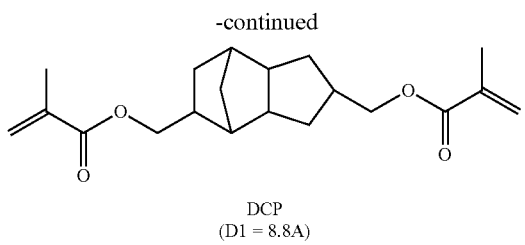

DCP
(D1 = 8.8A)

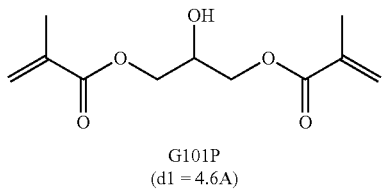

G101P
(d1 = 4.6A)

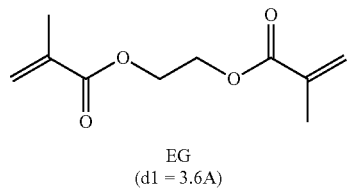

EG
(d1 = 3.6A)

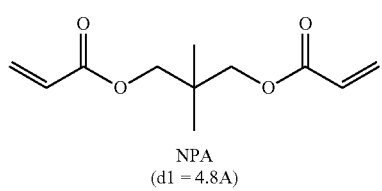

NPA
(d1 = 4.8A)

<Poly(meth)acrylic Monomer (C)>

The poly(meth)acrylic monomer (C) shown in Tables 1 to 3 (i.e., poly(meth)acrylic monomers having three or more (meth)acryloyloxy groups) are as follows.

TMPA: trimethylolpropane triacrylate, manufactured by Kyoeisha Chemical Co., Ltd.

A-TMMT: tetramethylolmethane tetraacrylate, manufactured by Shin-Nakamura Chemical Co., Ltd.

U15HA: 15-functional urethane acrylate, manufactured by Shin-Nakamura Chemical Co., Ltd.

<Photopolymerization Initiators>

The photopolymerization initiators shown in Tables 1 to 3 are as follows.

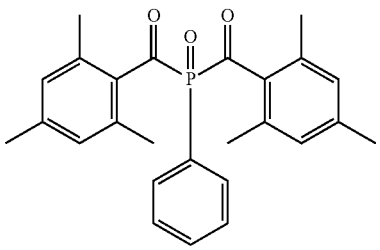

819

-continued

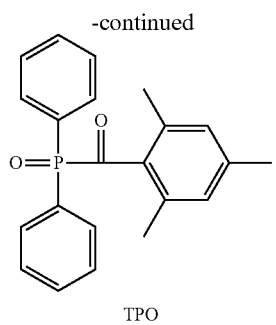

TPO

819: "OMNIRAD 819" (acylphosphine oxide compound), manufactured by IGM Resins B.V.

TPO: "OMNIRAD TPO" (acylphosphine oxide compound), manufactured by IGM Resins B.V.

As shown in Tables 1 to 3, the three-dimensional modeling products produced from the respective photocurable compositions of Examples, which had a storage modulus at 135° C. of $3.0 \times 10^8$ Pa or more, exhibited a superior dimensional accuracy after heat sterilization (i.e., a reduced deviation from the design value of the length L) as compared to the three-dimensional modeling products produced from the respective photocurable compositions of Comparative Examples, which had a storage modulus at 135° C. of less than $3.0 \times 10^8$ Pa.

[Evaluation of Crack Resistance of Cured Products]

Those instruments that are intraorally used, such as surgical guides and dental trays, are subjected to a force applied thereto in the oral cavity and during use, and thus required to have a certain crack resistance that can withstand such a force.

In view of this, a crack resistance test was conducted by the following method to evaluate the suitability for surgical guides, dental trays, and the like.

Using a DLP-type 3D printer (CARA PRINT 4.0, manufactured by Kulzer GmbH), a sheet-like modeling product of each photocurable composition shown in Table 4, which had a length of 64 mm, a width of 10 mm, and a thickness of 3.3 mm, was produced under conditions in which each layer was irradiated with visible light having a wavelength of 405 nm at a dose of 11 mJ/cm² in the direction in which the 64 mm×3.3 mm surface was in contact with the modeling table at a stacking width of 50 μm. The thus obtained sheet-like modeling product was irradiated with ultraviolet rays having a wavelength of 365 nm at a dose of 3 J/cm² to fully cure the photocurable composition, whereby a cured product P2 of a test piece was obtained.

To the thus obtained cured product P2, a load was applied until a deflection of 3 mm was obtained, using a tensile compression tester (210X, manufactured by INTESCO Co., Ltd.) in a three-point bending mode at a test temperature of 23° C., a fulcrum distance of 50 mm, and a cross head speed of 5 mm/min.

For each photocurable composition of interest, six test pieces were tested, and an evaluation of "A" was given when none of the six test pieces was cracked, an evaluation of "B" was given when one to four test pieces were cracked, or an evaluation of "C" was given when five or more test pieces were cracked. The results thereof are shown in Table 4.

<Di(meth)acrylic Monomer (X)>

The di(meth)acrylic monomer (X) shown in Table 4 [i.e., a di(meth)acrylic monomer which contains two (meth)acryloyloxy groups and a cyclic structure, and in which the d1 (i.e., the distance between an oxygen atom forming an oxy group in one of the (meth)acryloyloxy groups and an oxygen atom forming an oxy group in another of the (meth)acryloyloxy groups) is 17.0 Å or more] is SR540 among the above-described di(meth)acrylic monomer (A).

<Di(meth)acrylic Monomers (Y)>

The di(meth)acrylic monomers (Y) shown in Table 4 [i.e., di(meth)acrylic monomers which contain two (meth)acryloyloxy groups, and in which the d1 (i.e., the distance between an oxygen atom forming an oxy group in one of the (meth)acryloyloxy groups and an oxygen atom forming an oxy group in another of the (meth)acryloyloxy groups) is less than 17.0 Å] are SR348 among the above-described di(meth)acrylic monomer (A) and NP among the above-described di(meth)acrylic monomer (B).

In Table 4, the rows of "Mono(meth)acrylic monomer", "Poly(meth)acrylic monomer (C)", and "Photopolymerization initiator" have the same meanings as in Tables 1 to 3.

In Table 4, the numbers in the rows of the respective components, the blank boxes, and the row of "Storage modulus at 135° C. [Pa]" also have the same meanings as in Tables 1 to 3.

TABLE 4

| Components of photocurable composition | | | Example 4 | Example 6 | Example 14 | Example 23 | Example 25 |
|---|---|---|---|---|---|---|---|
| Mono(meth)acrylic monomer | PO | | 20 | | | | |
| | IBXA | | | | | 20 | |
| Di(meth)acrylic monomer (X) | SR540 | | | | 80 | | 75 |
| Di(meth)acrylic monomer (Y) | SR348 | | 80 | 80 | | | 25 |
| | NP | | | 20 | 20 | | |
| Poly(meth)acrylic monomer (C) | A-TMMT | | | | | 80 | |
| Photopolymerization initiator | TPO | | 2 | 2 | 2 | | |
| | 819 | | | | | 2 | 2 |
| Storage modulus at 135° C. [Pa] | | | 4.8E+08 | 1.4E+09 | 6.0E+08 | 3.1E+09 | 3.6E+08 |
| Evaluation of crack resistance | | | B | B | A | C | A |

While the crack resistance of the three-dimensional modeling product produced from the photocurable composition of Example 23, which had a storage modulus at 135° C. of more than $3.0 \times 10^9$ Pa, was evaluated as "C", the crack resistance was evaluated as "A" or "B" for the three-dimensional modeling products produced from the photocurable compositions of Examples 4, 6, 14, and 25, which had a storage modulus at 135° C. of $3.0 \times 10^9$ Pa or less.

The three-dimensional modeling products produced from the photocurable compositions of Examples 14 and 25, which contained the di(meth)acrylic monomers (X) and (Y), not only had a crack resistance evaluation of "A" as shown in Table 4 but also exhibited an excellent dimensional accuracy after the heat sterilization as shown above in Table 2. On the other hand, the three-dimensional modeling products produced from the photocurable compositions of Examples 4 and 6, which did not contain the di(meth)acrylic monomer (X), had a crack resistance evaluation of "B" as shown in Table 4, although they exhibited an excellent dimensional accuracy after the heat sterilization as shown above in Table 1.

The disclosure of Japanese Patent Application No. 2020-117229 filed on Jul. 7, 2020 is hereby incorporated by reference in its entirety.

All the documents, patent applications, and technical standards that are described in the present specification are hereby incorporated by reference to the same extent as if each individual document, patent application, or technical standard is concretely and individually described to be incorporated by reference.

The invention claimed is:

1. A photocurable composition, comprising a photopolymerizable component and a photopolymerization initiator, wherein:
in a case in which a rectangular sheet-like test piece P1 with a length of 40 mm, a width of 10 mm, and a thickness of 0.5 mm is produced by photomodeling under conditions in which the photocurable composition is irradiated with visible light having a wavelength of 405 nm at an irradiation dose of 11 mJ/cm$^2$ to form a cured layer P1 with a thickness of 50 µm, the cured layer P1 is stacked in a thickness direction thereof to form a rectangular sheet-like modeling product P1 with a length of 40 mm, a width of 10 mm, and a thickness of 0.5 mm, and the modeling product P1 is irradiated with ultraviolet rays having a wavelength of 365 nm at an irradiation dose of 3 J/cm$^2$ to produce the test piece P1, and a storage modulus is measured for the thus produced test piece P1 by dynamic viscoelastic measurement with a measurement frequency of 1 Hz while increasing a temperature in a range of from 25° C. to 300° C. at a rate of 3° C./min, the storage modulus at 135° C. is $3.0 \times 10^8$ Pa or more;
in a case in which
a distance between an oxygen atom forming an oxy group in one of (meth)acryloyloxy groups and an oxygen atom forming an oxy group in another of (meth)acryloyloxy groups in a di(meth)acrylic monomer is determined as d1,
a di(meth)acrylic monomer which comprises two (meth)acryloyloxy groups and a cyclic structure, and has the d1 of 15.0 Å or more is determined as a di(meth)acrylic monomer (A), and a di(meth)acrylic monomer which comprises two (meth)acryloyloxy groups, and has the d1 of less than 15.0 Å is determined as a di(meth)acrylic monomer (B),
the photopolymerizable component comprises,
two kinds of the di(meth)acrylic monomer (A) that are different in the d1, or the di(meth)acrylic monomer (A), and at least one of a mono(meth)acrylic monomer (D), which comprises one (meth)acryloyloxy group and at least one of a branched structure or a cyclic structure, or the di(meth)acrylic monomer (B);
and wherein,
a content of the di(meth)acrylic monomer (A) is 75% by mass or more, with respect to a total amount of all of (meth)acrylic monomers contained in the photocurable composition.

2. The photocurable composition according to claim 1, wherein the storage modulus at 135° C. is $3.5 \times 10^9$ Pa or less.

3. A photocurable composition, comprising a photopolymerizable component and a photopolymerization initiator, wherein:
in a case in which a rectangular sheet-like test piece P1 with a length of 40 mm, a width of 10 mm, and a thickness of 0.5 mm is produced by photomodeling under conditions in which the photocurable composition is irradiated with visible light having a wavelength of 405 nm at an irradiation dose of 11 mJ/cm$^2$ to form a cured layer P1 with a thickness of 50 µm, the cured layer P1 is stacked in a thickness direction thereof to form a rectangular sheetlike modeling product P1 with a length of 40 mm, a width of 10 mm, and a thickness of 0.5 mm, and the modeling product P1 is irradiated with ultraviolet rays having a wavelength of 365 nm at an irradiation dose of 3 J/cm$^2$ to produce the test piece P1, and a storage modulus is measured for the thus produced test piece P1 by dynamic viscoelastic measurement with a measurement frequency of 1 Hz while increasing a temperature in a range of from 25° C. to 300° C. at a rate of 3° C./min, the storage modulus at 135° C. is $3.0 \times 10^8$ Pa or more;
in a case in which
a distance between an oxygen atom forming an oxy group in one of (meth)acryloyloxy groups and an oxygen atom forming an oxy group in another of (meth)acryloyloxy groups in a di(meth)acrylic monomer is determined as d1,
a di(meth)acrylic monomer which comprises two (meth)acryloyloxy groups and a cyclic structure, and has the d1 of 17.0 Å or more is determined as a di(meth)acrylic monomer (X), and a di(meth)acrylic monomer which comprises two (meth)acryloyloxy groups and a cyclic structure, and has the d1 of 15.0 Å or more and less than 17.0 Å is determined as a di(meth)acrylic monomer (Y),
the photopolymerizable component comprises the di(meth)acrylic monomer (X) and the di(meth)acrylic monomer (Y);
and wherein,
a total content of the di(meth)acrylic monomer (X) and the di(meth)acrylic monomer (Y) is 80% by mass or more with respect to a total amount of all of (meth)acrylic monomers contained in the photocurable composition.

4. The photocurable composition according to claim 3, wherein a content of the di(meth)acrylic monomer (X) is from 50% by mass to 90% by mass with respect to a total amount of (meth)acrylic monomer components.

5. The photocurable composition according to claim 3, wherein a content of the di(meth)acrylic monomer (Y) is from 10% by mass to 50% by mass with respect to a total amount of (meth)acrylic monomer components.

6. The photocurable composition according to claim 1, having a viscosity, which is measured by an E-type viscometer under conditions of 25° C. and 50 rpm, of from 5 mPa's to 6,000 mPa·s.

7. The photocurable composition according to claim 1, which is a photocurable composition for photomodeling.

8. The photocurable composition according to claim 1, which is used for production of a dental product by photomodeling.

9. A three-dimensional modeling product, which is a cured product of the photocurable composition according to claim 1.

10. A dental product, comprising the three-dimensional modeling product according to claim 9.

11. The dental product according to claim 10, which is a dental surgical guide, a dental tray, a mouthpiece, or a dental model.

* * * * *